US00PP17971P3

(12) United States Plant Patent
Jandrew

(10) Patent No.: US PP17,971 P3
(45) Date of Patent: Aug. 28, 2007

(54) ***PENSTEMON* PLANT NAMED 'PHENI ABLOS'**

(50) Latin Name: *Penstemon hartwegii*
Varietal Denomination: Pheni Ablos

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 8 days.

(21) Appl. No.: 11/302,477

(22) Filed: Dec. 13, 2005

(65) Prior Publication Data

US 2007/0136916 P1 Jun. 14, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Georgia Helmer
(74) *Attorney, Agent, or Firm*—Jondle & Associates P.C.

(57) ABSTRACT

A new *Penstemon* plant particularly distinguished by large white flowers with light pink margins, large inflorescences, early flowering, grass-green foliage with lanceolate leaves, vigorous growth, and a relatively compact, steady, and upright plant habit with good branching ability is disclosed.

2 Drawing Sheets

Genus and species: *Penstemon hartwegii* Benth.
Variety denomination: 'Pheni Ablos'.

BACKGROUND OF THE NEW PLANT

The present invention comprises a new and distinct cultivar of *Penstemon,* botanically known as *Penstemon hartwegii,* and hereinafter referred to by the cultivar name 'Pheni Ablos'. The new cultivar originated from a hybridization made in 2002 in Gilroy, Calif. The female parent is a proprietary *Penstemon* plant designated '108-1' (unpatented) having scarlet flowers, and the male parent is a proprietary *Penstemon* plant designated '112-1' (unpatented) having lavender flowers. The seeds produced by the hybridization were sown in November 2002, and the resulting seedlings were selected in May 2003. A single plant selection was chosen for further evaluation and for asexual propagation in the summer of 2003.

The new cultivar was created in 2002 in Gilroy, Calif. and has been asexually reproduced repeatedly by vegetative cuttings and tissue culture in Gilroy, Calif. over a three-year period. The plant has also been trialed at Gilroy, Calif., and Hillscheid, Germany. The present invention has been found to retain its distinctive characteristics through successive asexual propagations.

Plant Breeder's Rights for this cultivar were applied for in Europe on Oct. 14, 2005 and in Canada on Mar. 29, 2005.

SUMMARY OF THE INVENTION

The following are the most outstanding and distinguishing characteristics of this new cultivar when grown under normal horticultural practices in Gilroy, Calif. and Hillscheid, Germany.

1. Large white flowers with light pink markings;
2. Large inflorescences;
3. Early flowering;
4. Grass-green foliage with lanceolate leaves;

5. Vigorous growth; and
6. An upright, robust and relatively compact and steady plant habit with good branching ability.

DESCRIPTION OF PHOTOGRAPHS

This new *Penstemon* plant is illustrated by the accompanying photographs which show blooms, buds, and foliage of the plant in full color; the colors shown are as true as can be reasonably obtained by conventional photographic procedures. The photographs are of whole plants about 3 months old, grown in a field in Gilroy, Calif. in mid-July 2005.

DESCRIPTION OF THE NEW CULTIVAR

Figure 1:
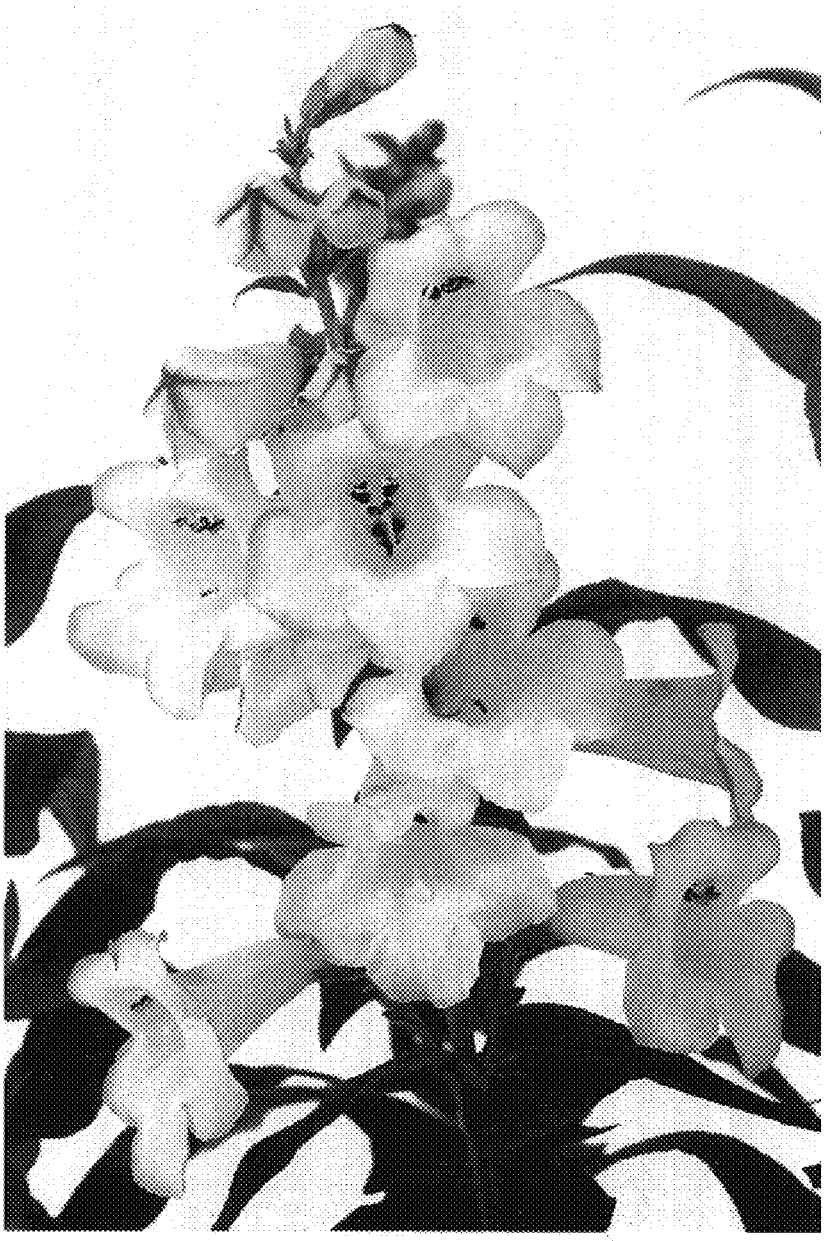
FIG. 1 shows a close-up of the mature inflorescences.
Figure 2:
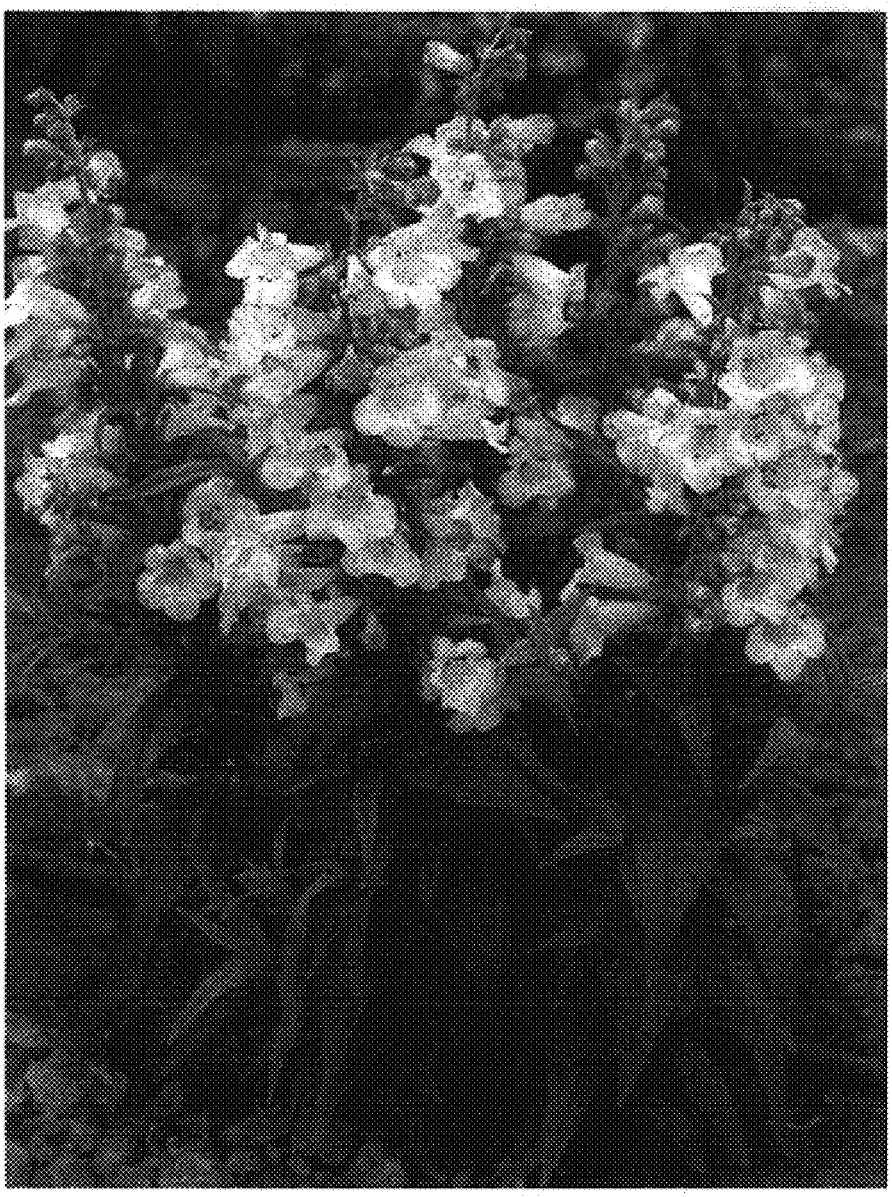
FIG. 2 shows the overall plant habit, including blooms, buds, mature foliage, and plant habit.

The following detailed descriptions set forth the distinctive characteristics of 'Pheni Ablos'. The data which define these characteristics were collected from asexual reproductions carried out in Gilroy, Calif. The plant history was taken on nine to eleven-week-old plants grown in Hillscheid, Germany in 2005. Rooted cuttings were planted into 12-cm plastic pots placed in a greenhouse. The plants were not pinched, so they mostly developed into single-stem plant habits. Most observations were made after nine to ten weeks at the beginning of flowering. Color readings were taken under natural light. Color references are primarily to The R.H.S. Colour Chart of The Royal Horticultural Society of London (R.H.S.) (2001 edition).

DETAILED BOTANICAL DESCRIPTION OF THE NEW PLANT

Classification:
*Family.*—Scrophulariaceae.
*Botanical name.*—*Penstemon hartwegii* Benth.

Parentage:

*Female parent.*—'108-1' a proprietary scarlet-flowered *Penstemon* plant (unpatented).

*Male parent.*—'112-1' a proprietary lavender-flowered *Penstemon* plant (unpatented).

Growth:

*Form.*—Herbaceous perennial; suffrutescent; tolerates only slight frost; usually cultivated as an annual plant.

*Habit.*—Un-pinched plants develop a flowering main stem with only very short secondary branches at the nodes; for commercial purposes, the young plants are usually pinched so that 5–10 stems of equal size will develop.

*Height.*—73 cm for a 9-week-old single-stem plant as measured from the soil to the tip, including the inflorescence.

*Width.*—18 cm.

*Time to produce a finished flowering plant.*—11 weeks for a single-stem plant in a 5-inch pot (spring cultivation); about 13–14 weeks for a branched plant.

*Outdoor plant performance.*—Use in garden beds or in container planting.

*Time to initiate and develop roots.*—21 days.

*Root description.*—Somewhat fleshy at the base, mainly fibrous, and self-branching.

Leaves:

*Arrangement.*—Opposite and decussate.

*Shape.*—Lanceolate.

*Apex.*—Acute to acuminate.

*Base.*—Sessile.

*Margin.*—Very weakly crenate with fine, short bristles.

*Immature.*—Color: Upper surface: RHS 143B. Lower surface: RHS 138B. Texture: Smooth.

*Mature* (*fully expanded*).—Length: 13.0 cm. Width: 4.5 cm. Color: General: Medium green to grass green. Upper surface: RHS 137D to RHS 143A. Lower surface: Between RHS 138A and RHS 138B. Texture: Leathery, glabrous, and slightly glossy. Venation: Type: Pinnate; with the midrib of the lower side protruding. Color: RHS 145C on the lower side.

Stems:

*Length.*—49 cm as measured from the base (not including the inflorescence).

*Diameter.*—0.6 cm as measured at the midpoint.

*Internode length.*—5 cm.

*Color.*—RHS 145A.

*Texture.*—Appears smooth, with sparse, fine pubescence.

*Anthocyanin.*—Absent.

Flower bud:

*Shape.*—Tube-shaped with a closed end.

*Diameter.*—1.5 cm.

*Length.*—3.5 cm.

*Color* (*at tight bud*).—Mainly RHS 2C (pale light yellow) with RHS 52B (pink) markings at the tip.

Inflorescence:

*Inflorescence type.*—Thyrse (but appears as a terminal raceme at the start of flowering) with short peduncles emerging at the nodes in opposite arrangement, each peduncle bearing 3–4 flowers or buds at various stages of development; the flowers are horizontally or somewhat downward directed.

*Blooming habit.*—Intermittent; removing of spent inflorescences enhances new flowering.

*Quantity of inflorescence per plant.*—One per plant (for single stem plants) and 5–10 per plant (for pinched plants).

*Lastingness of individual blooms on the plant.*—5–6 days at 20° C.

*Fragrance.*—None.

*Inflorescence length.*—Approximately 30–33 cm (more than one-third of the total height).

*Inflorescence diameter.*—Approximately 10 cm.

*Penduncle.*—Color: RHS 145A (light green). Length: Up to 4 cm. Diameter: 0.25 cm. Texture: Pubescent.

Flower:

*Type.*—Zygomorphic; funnel-shaped, 5-lobed at the free end with the lobes outward directed and somewhat wavy.

*Floret quantity* (*per inflorescence*).—About 25–30.

*Shape.*—Funnel-shaped.

*Floret diameter.*—3.8 cm.

*Floret length.*—4.0 cm.

*Color.*—General: White with light pink edges. Corolla lobes (frontal view): RHS 155A, with a narrow margin of RHS 62C. Funnel (outer surface): RHS 155A. Corolla (inside color): RHS 150D.

*Petals* (*lobes*).—Quantity: 5. Arrangement: Two upper lobes with two lateral lobes and one lower lobe. Apex: Rounded. Base: Fused and funnel-shaped. Margin: Entire. Texture: Smooth.

*Upper lobes, size.*—Length (from the Corolla opening): 1.3 cm. Width: 1.6 cm.

*Lateral lobes, size.*—Length (from the Corolla opening): 1.4 cm. Width: 1.7 cm.

*Lower lobe.*—Length (from the Corolla opening): 1.3 cm. Width: 1.6 cm.

*Sepals.*—Quantity: 5. Color: RHS 143B (green). Length: 0.8 cm. Width: 0.5 cm. Shape: Ovate with a pointed tip. Apex: Acute. Base: Attenuate. Anthocyanin: Absent. Texture: A little rough and pubescent (covered with short, fine hair).

*Pedicels.*—Color: RHS 145A (light green). Length: 0.6 cm. Diameter: 0.1 cm. Texture: Pubescent (covered with short hair).

Reproductive organs:

*Stamens.*—Quantity: 5 total, of which 4 are fertile. Filament: Color: RHS 155D (white). Length: 2.6–3.1 cm. Diameter: 0.1 cm. Anther color: RHS N186C (dark purple). Pollen amount: Abundant. Pollen color: RHS 4D (pale yellow).

*Pistils.*—Quantity: 1. Length: 3.1 cm. Stigma color: RHS 145D (greenish-white). Style color: RHS 155D (white).

Fruit and seed set: Plants are fertile; frequently, the ovary is ovate and 0.6 cm in length, 0.4 cm in diameter; when the corolla drops, the ovary develops into a seed capsule (ovate in shape) of about 1.1 cm in length and 0.7 cm in diameter.

*Seed.*—Color: RHS 200B. Shape: Irregularly round (a few more oblong), wrinkled and pitted. Diameter: 0.15 cm.

Disease and insect resistance: Has not been observed.

COMPARISON WITH PARENTAL AND COMMERCIAL CULTIVARS

'Pheni Ablos' differs from the female parent, proprietary *Penstemon* plant '108-1' (unpatented), in that 'Pheni Ablos' has mainly white flowers, while '108-1' has scarlet flowers.

Additionally, 'Pheni Ablos' has a somewhat deeper green foliage and a more compact plant habit than '108-1'.

'Pheni Ablos' differs from the male parent, proprietary *Penstemon* plant '112-1' (unpatented), in that 'Pheni Ablos' has mainly white flowers, while '112-1' has lavender flowers. Additionally, 'Pheni Ablos' flowers earlier and has a more compact plant habit than '112-1'.

'Pheni Ablos' differs from the commercial cultivar 'Cathedral Hot Rose' (patent status unknown) in that 'Pheni Ablos' has lighter pink flowers with strong red markings than 'Cathedral Hot Rose'. Additionally, 'Pheni Ablos' has a more compact plant habit and flowers earlier than 'Cathedral Hot Rose'.

I claim:

1. A new and distinct cultivar of *Penstemon* plant as shown and described herein.

* * * * *